(12) United States Patent
Stevens

(10) Patent No.: US 6,193,735 B1
(45) Date of Patent: Feb. 27, 2001

(54) COMBINED ROTARY AND AXIAL RECIPROCATING GUIDE WIRE

(76) Inventor: Robert C. Stevens, 18265 NW. Highway 335, Williston, FL (US) 32696

( * ) Notice: Subject to any disclaimer, the term of this patent is extended or adjusted under 35 U.S.C. 154(b) by 0 days.

(21) Appl. No.: 08/714,194

(22) Filed: Sep. 16, 1996

(51) Int. Cl.[7] .................................................. A61B 17/22
(52) U.S. Cl. .......................................... 606/159; 600/585
(58) Field of Search .................................... 606/157, 180, 606/171; 128/652, 772; 604/164, 280; 600/434, 585

(56) References Cited

U.S. PATENT DOCUMENTS

| | | |
|---|---|---|
| 4,749,376 * | 6/1988 | Kensey et al. ........................ 606/159 |
| 4,854,325 | 8/1989 | Stevens . |
| 4,936,845 | 6/1990 | Stevens . |
| 5,116,350 | 5/1992 | Stevens . |
| 5,234,451 * | 8/1993 | Osypka ................................. 606/159 |
| 5,431,673 * | 7/1995 | Summers et al. ..................... 606/171 |
| 5,490,859 * | 2/1996 | Mische et al. ........................ 606/159 |

* cited by examiner

Primary Examiner—William E. Kamm
Assistant Examiner—George R. Evanisko
(74) Attorney, Agent, or Firm—Fay, Sharpe, Fagan, Minnich & McKee, LLP

(57) ABSTRACT

Apparatus for opening an obstructed region of a patient blood vessel comprising a catheter and guidewire. The guidewire is of sufficient length to extend from a region outside the patient to the obstructed region. The catheter acts as a guide tube supporting the guidewire for free axial and rotary movement. A power assembly is positioned outside the patient and has an output shaft joined to the guidewire. The power assembly further includes plural motors drivingly interrelated to move the output shaft to impart simultaneous axial reciprocation and rotary reciprocation to guidewire.

26 Claims, 4 Drawing Sheets

COMBINED ROTARY AND AXIAL RECIPROCATING GUIDE WIRE

BACKGROUND OF THE INVENTION

The subject invention is directed to a catheter system and apparatus for opening a totally or partially occluded blood vessel.

In my prior U.S. Pat. Nos. 4,936,845, issued Jun. 26, 1990, for "Catheter System Having Distal Tip For opening Obstructions," and 5,116,350, issued May 26, 1992, under the same title, I have disclosed methods and apparatus for opening an occluded blood vessel through the use of a catheter with a drive shaft having a distal tip portion that is impinged against the occlusion with an axial or rotary reciprocatory motion. The patents disclose two separate devices, one capable of producing an axially reciprocated movement and the other capable of producing a rotary reciprocal movement.

There are numerous other arthrectomy devices for opening vascular obstructions such as the Kinsey catheter disclosed in U.S. Pat. No. 4,749,376. These other prior devices that use rotary rotation all have the common problem of "wrapping" or "twisting" tissue because of the unidirectional rotation. The reciprocal rotation of my device prevents this from happening.

In my prior U.S. Pat. No. 4,854,325, issued Aug. 8, 1989, for "Reciprocating Guidewire Method," I have disclosed the use of a conventional guidewire for use in forming a passageway through a vascular obstruction. This system utilizes a conventional guidewire and catheter which is already in the patient's vascular system, such as in a coronary artery. This patent discloses a system for reciprocating the guidewire back and forth.

It now appears that it would be most desirable if the drive shaft tip or the guidewire tip were subjected to both forms of reciprocation (i.e., axial and rotary) simultaneously. The combined motions seem to produce more efficient and effective opening of the occlusions than either motion performed by itself.

SUMMARY OF THE INVENTION

The subject invention provides a system and apparatus that produces combined axial and rotary reciprocatory movements of the drive shaft tip or the guidewire tip in an effective, controllable manner.

My prior U.S. Pat. Nos. 4,936,845 and 5,116,350, issued Jun. 26, 1990 and May 26, 1992, respectively, are dedicated systems with a single purpose and are meant for use in the larger vessels. The disclosure of these patents are incorporated herein by reference. Briefly, however, the catheter system generally comprises the previously-mentioned drive catheter wire which terminates in a distal tip that can have a variety of known configurations to assist in penetration through obstructions such as plaque in the blood vessel to be opened. Typical designs are shown, for example, in my above-mentioned prior U.S. patents.

My prior U.S. Pat. No. 4,854,325, issued Aug. 8, 1989, titled "Reciprocating Guidewire Method" now appears to be the preferred method and will be the method described in detail. The apparatus generally comprises a conventional catheter having a guidewire protruding from the tip of the catheter. The guidewire has a sufficient length to extend from a region outside a patient to the obstructed region. The catheter acts as a guide for free axial and rotary movement. Positioned outside the patient are power means including an output shaft coupled to the guidewire. The power means includes plural motor means for simultaneously axially reciprocating and rotating the guidewire to impart simultaneous axial reciprocation and rotary reciprocation to the guidewire.

In addition, and in accordance with a further aspect of the invention, there are means provided for varying the rate of axial reciprocation imparted to the guidewire. Also, it is preferable that the power means includes a first motor for rotating the guidewire and a second motor for axially reciprocating the guidewire. Means are also provided for periodically reversing the direction of rotation of the first motor to produce rotary reciprocation of the guidewire.

In its preferred form, the first motor is mounted for reciprocation and the second motor is drivingly connected to cause axial reciprocation of the first motor.

As can be seen from the foregoing, a primary object of the invention is the provision of a catheter system and apparatus that can produce combined axial and rotary reciprocatory movements of the guidewire in a manner to facilitate opening of obstructions in a patient's blood vessels.

A further object of the invention is the provision of an apparatus of the type described wherein the rate of axial reciprocation can be readily varied without varying the rate of rotary reciprocation.

A still further object is the provision of an apparatus of the general type discussed which is relatively simple to use, and efficient and effective in operation. The use of a guidewire in place of a drive shaft with tip is very desirable. By using a guidewire to do both the axial and rotary reciprocatory movements, no change of catheter or other device is necessary during a procedure. In other words, the angiographic catheter and the guidewire are already in the patient's vascular system (example: a coronary artery). If the attempted angiographic study or angioplasty is successful, there is no need for additional devices. However, when an obstruction is encountered that cannot be crossed with the conventional catheter and guidewire which is being used in the patient, additional help is needed. Having to remove the catheter and guidewire already in the patient and exchanging it for another system doubles the risk to the patient.

With my new system, all you need is to attach the guidewire, which is already in the patient, to the external motorized device in order to impart the axial and rotary reciprocating movements.

Another advantage to the new system is in placing the guidewire and catheter at the beginning of the procedure. There are multiple branching vessels in the coronary system. Pushing a guidewire (0.014" in dia) with a very flexible ("floppy") tip section is difficult at best. We are talking about a 6 foot long guidewire being pushed through a catheter not much larger than the guidewire itself. The guidewire must also be able to be turned from side to side. Physical things, such as guidewires, at rest tend to remain at rest. However, if the guidewire is in motion such as being moved backward and forward and from side to side in a controlled manner, the guide will be easier to advance when the desired vessel opening is reached.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

Figure 1:
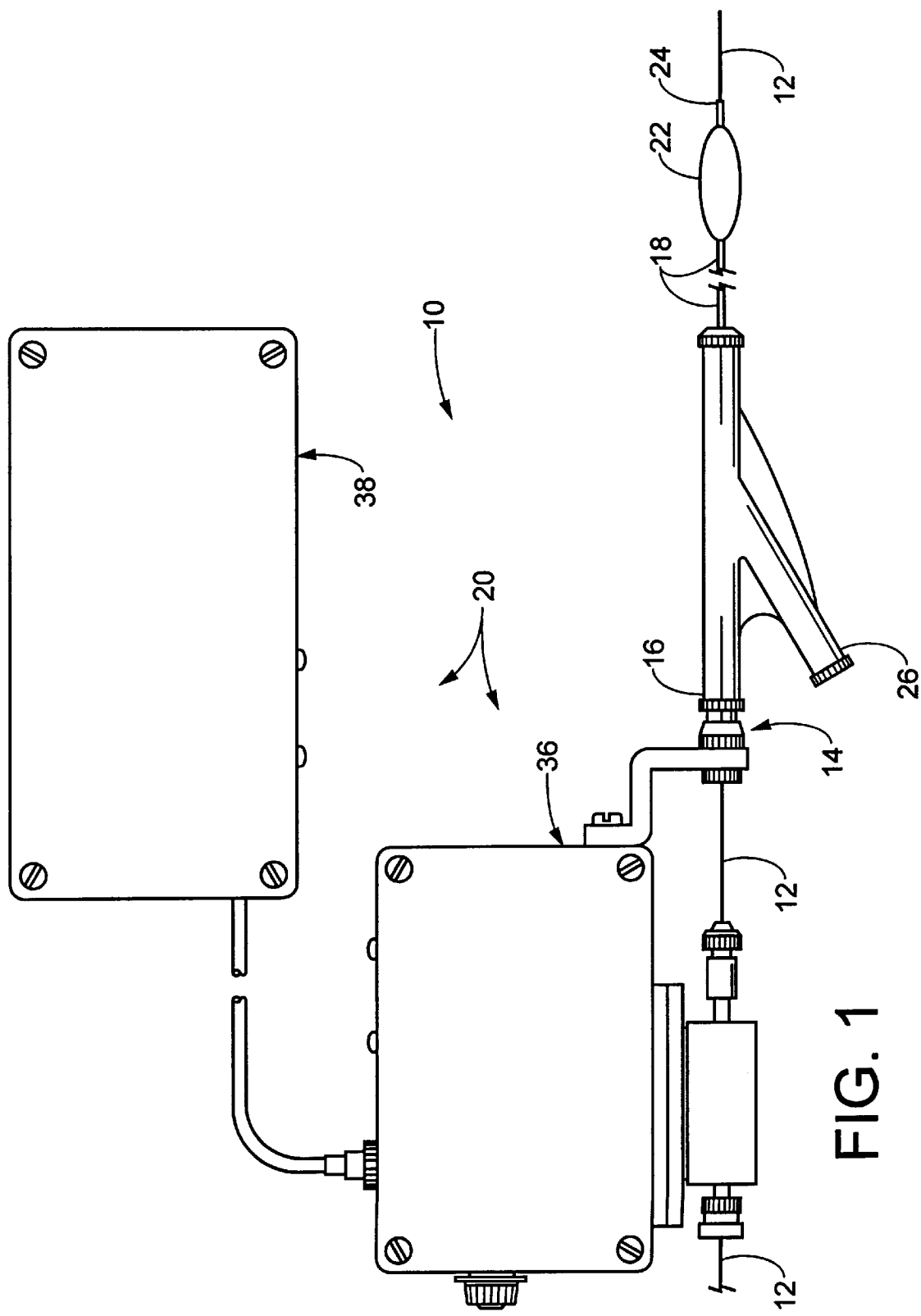
FIG. 1 is a pictorial view showing a catheter guidewire system formed in accordance with the preferred embodiment of the invention.

Referring now to the drawings wherein the showings are for the purposes of illustrating the preferred embodiment of the invention only and not for purposes of limiting same, FIG. 1 shows the overall arrangement of a catheter guidewire system 10 incorporating a power apparatus 20 for producing combined rotary reciprocation and axial reciprocation of a guidewire 12. The catheter shown is a coronary dilation catheter. The design is widely known and used. The guidewire 12 shown is also of common design used with coronary dilation catheters. At present, the coronary dilation procedure is the most likely to use the simultaneous axial-rotary reciprocating system.

The guidewire 12 extends outwardly through a hemostasis valve 14, which controls blood loss through a Y luer hub 16 configuration which is the proximal part of the coronary dilation catheter 18. The guidewire enters the straight section of the Y through the entire catheter 18, through the dilation balloon 22 portion and protrudes beyond the distal tip 24 portion of the coronary dilation catheter. The branching section of the Y which has a luer fitting 26 is used to inflate and deflate the balloon 22 as necessary.

Of particular importance to the subject invention, however, is the means by which the guidewire 12 can be subjected to both rotary reciprocation and axial reciprocation through the action of the power unit 20. In its preferred form, the power unit 20 includes two separate housings 36 and 38. The housing 36 carries the power means for imparting the axial reciprocation to the drive catheter 12, whereas the housing 38 carries suitable batteries and control means for producing the reverse of current supplied to one of the motors which imparts the reciprocatory rotary motion in a manner subsequently to be described. For the present, however, attention is directed to FIGS. 2 and 4 which best illustrate the housing 36 and the power means carried thereby. In particular, the housing 36 is a rigid molded plastic housing having a forward end 39 that carries an outwardly and downwardly extending bracket member 40. The lower end of the bracket member 40 carries a hemostasis valve 14 through which the drive catheter 12 extends. The outer or forward end of the fitting 14 is arranged to receive in a friction fit manner the end of the coronary dilation catheter.

Carried within the housing 36 is a conventional direct current rotary motor 44 positioned so that its output shaft 44a extends downwardly through the bottom wall 39a of the housing 36. Also contained within the housing 36 is a battery 46 and an on/off slide switch 48 that are connected through a rheostat type DC motor controller 49 in the manner best illustrated in FIG. 4. This arrangement allows the speed of rotation of the motor output of shaft 44a to be selectively varied.

Figure 2:
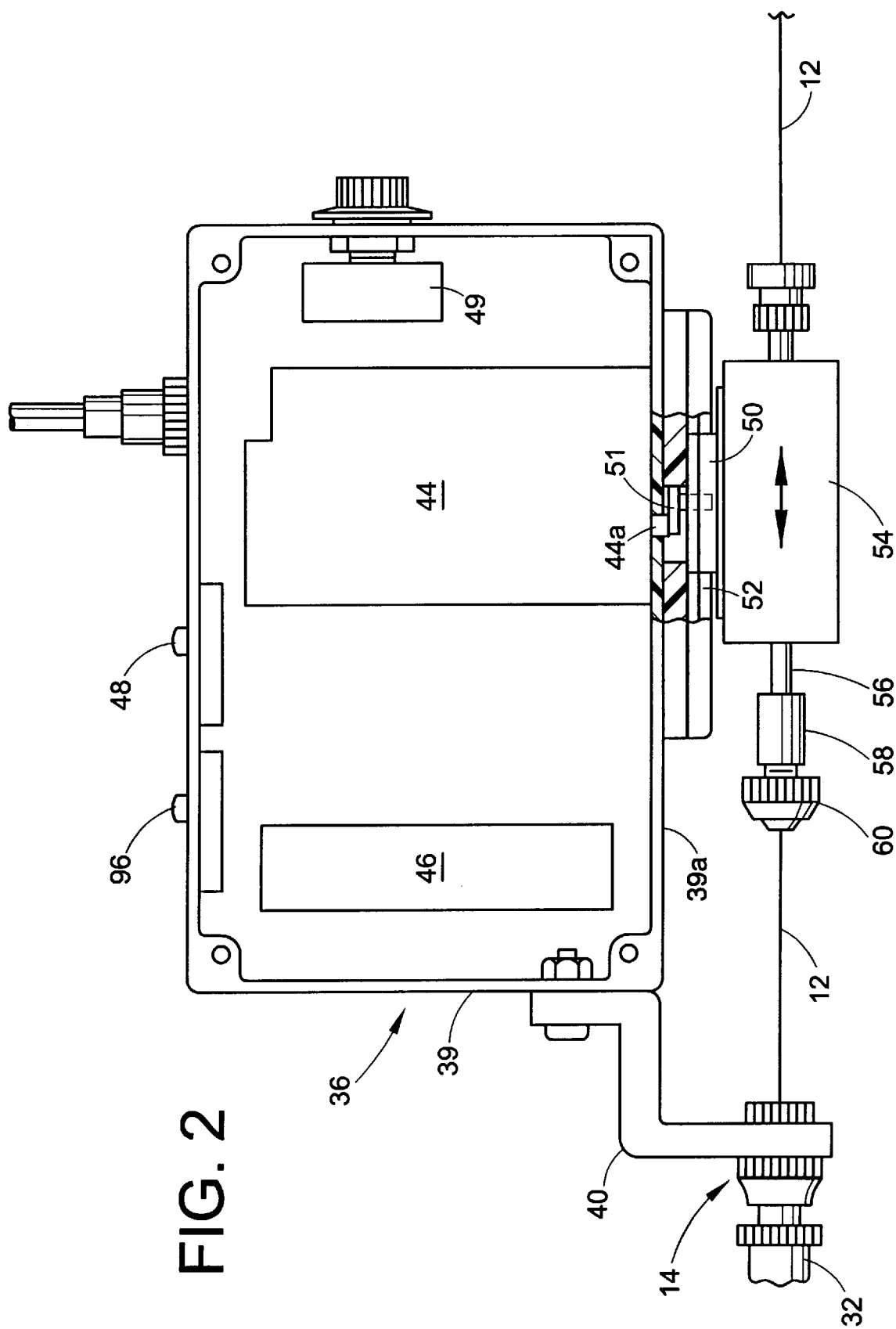
FIG. 2 is a view showing a portion of the catheter reciprocating apparatus (a side panel has been removed to show certain details of construction with the wiring omitted)

The output shaft 44a of motor 44 is connected through a crank arm 48 with a slide member 50 carried for reciprocation in suitable guides 52 mounted on the underside of the lower wall 39a as best seen in FIG. 2. These slides are arranged so as to allow free sliding movement of the slide member 50 in directions shown by the arrow upon rotation of the crank 48.

Suspended from the slide plate 50 is a second motor 54. Motor 54 is also a DC motor and has an output shaft 56 extending therethrough. The output shaft 56 is hollow and provides a path through which the guidewire 12 can extend. At the left-hand end of shaft 56 (as viewed in FIG. 2), there is a collet-like member 60 which joins to the shaft with a first portion 58 and has a resilient internal collar portion that is compressed into frictional gripping engagement with the guidewire 12 by an outer nut member 60. By tightening member 60 on the end portion 58, the shaft 56 is drivingly engaged with the guidewire 12. Thus, during rotation of motor 44, the motor 54 is caused to reciprocate as shown by the arrows imparting a reciprocatory motion to the guidewire 12. If, simultaneously therewith, motor 54 is driven to rotate member 60, a simultaneous rotary motion and axial reciprocation is applied to the guidewire 12. According to the subject invention, means are also provided to cause a reversal in the direction of rotation of the motor 54 so as to impart a reciprocatory rotary motion to member 60 and, in turn, the guidewire 12.

Figure 3:
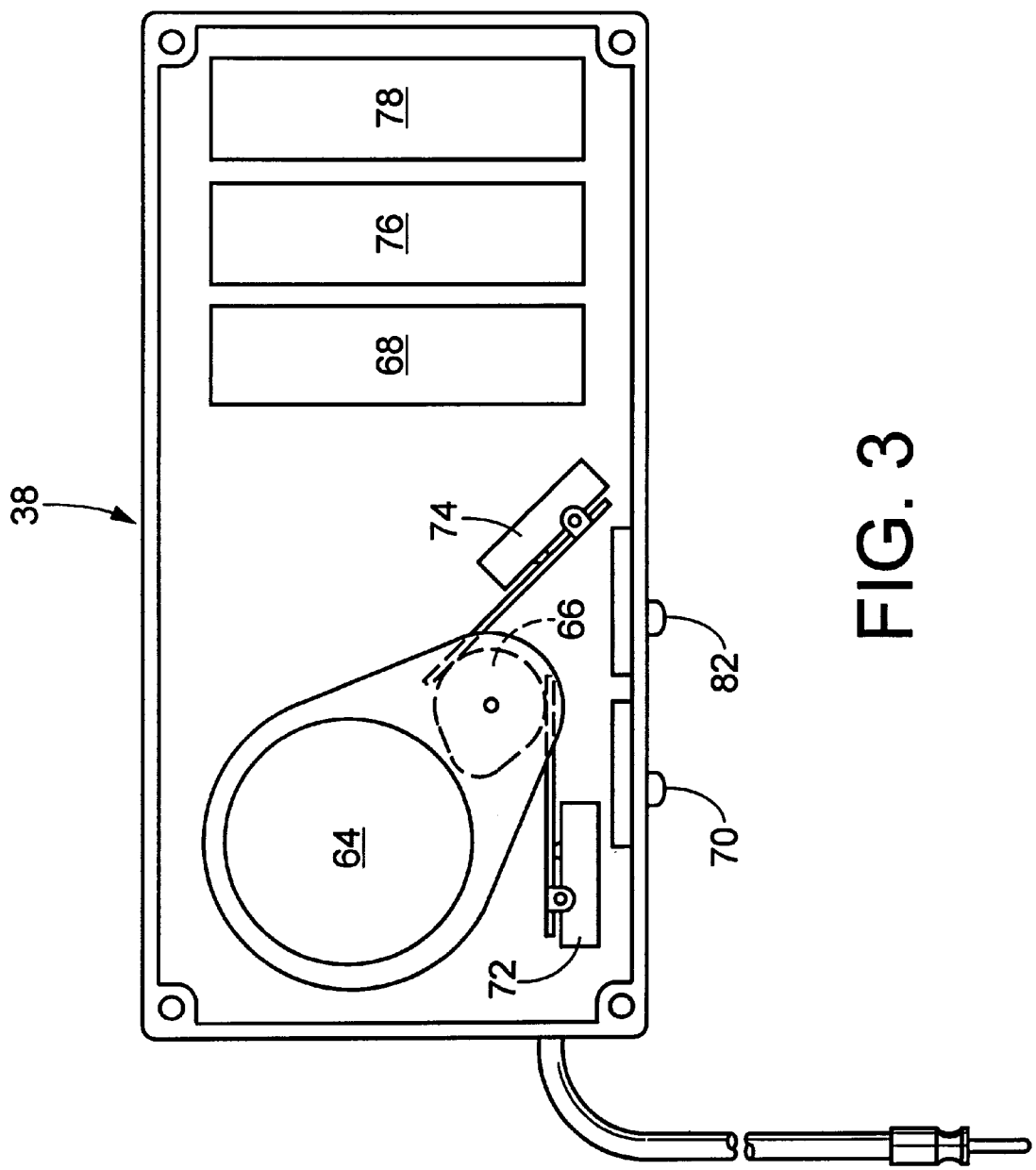
FIG. 3 is a view showing the interior of the apparatus (the wiring is omitted) used for producing rotary reciprocation of the apparatus; and, FIG. 4 is a somewhat diagrammatic showing of the wiring and controls used in the apparatus.
Figure 4:
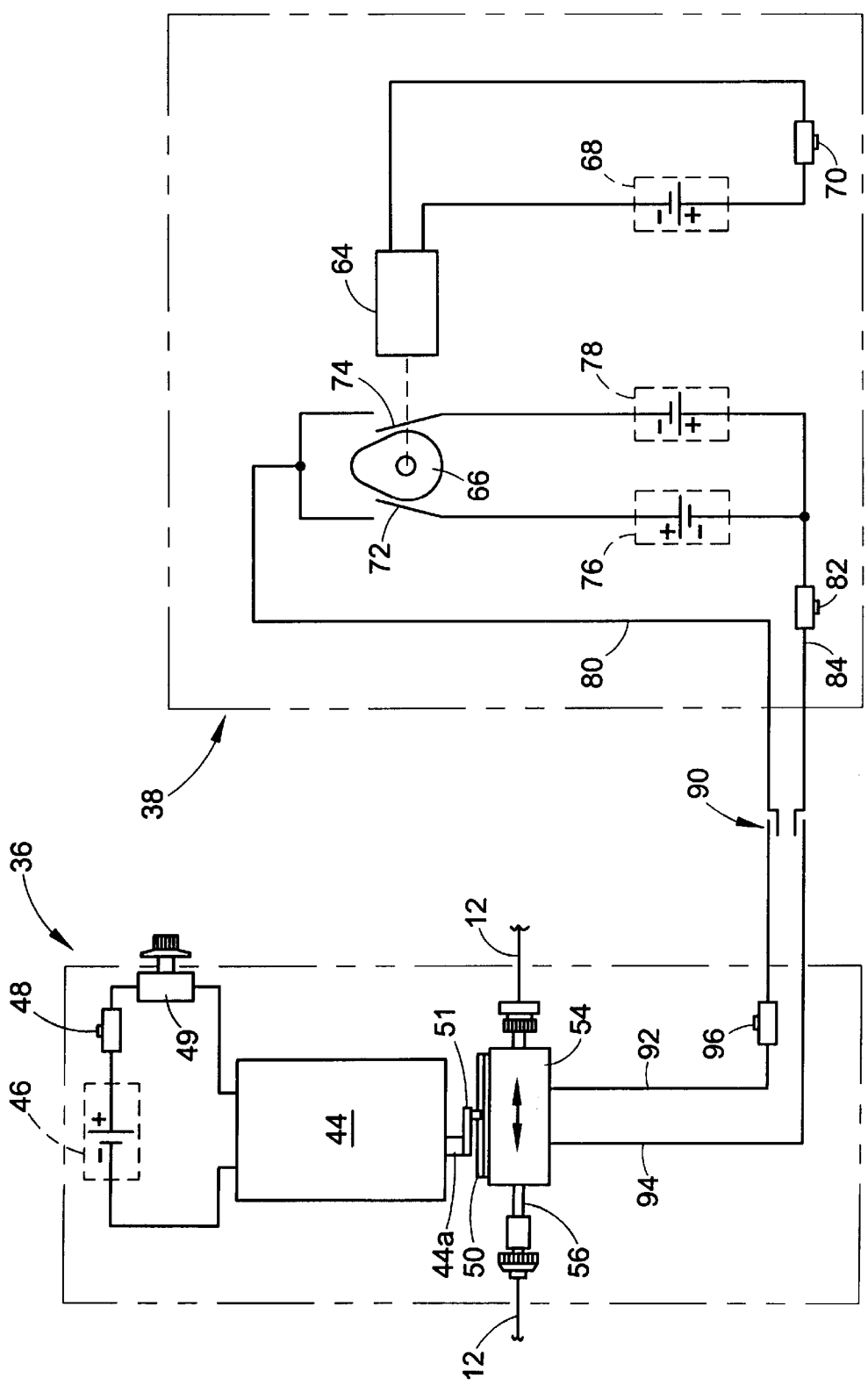

The means used to produce the reversal of current flow to the small DC motor 54 could, of course, be housed in the same housing 36 as houses the main reciprocating drive motor 44. It is preferred, however, to provide a separate housing 38 for these components. Referring in particular to FIG. 3 and 4, the means used for causing reversal of the motor 54 comprises a DC motor 64 that has its output shaft connected to rotate a cam 66. As shown in FIG. 3, the motor 64 is connected with the cam 66 through suitable reduction gearing (not shown). The motor 64 is connected with a battery 68 through a manual slide switch 70 as illustrated.

Referring again to the cam 66, this cam is positioned and arranged to rotate and alternately close and permit opening of two separate micro-switches 72 and 74. The micro-switches 72, 74 alternately complete and open circuits from two separate DC batteries 76 and 78 so that there is a constant reversal in polarity of the current supplied through a current source line 80. A suitable slide-type on/off switch 82 is included in a line 84 which completes the circuit through the micro-switches 72, 74. As shown, the lines 80 and 84 are connected through a standard coaxial plug assembly 90 to wires 92, 94, respectively. These wires, although not shown in FIG. 2, are connected with the motor 54. As can be appreciated, the rotation of the cam 66 thus supplies current of a constantly reversing polarity to the motor 54 to cause it to rotate in alternate directions. By controlling the speed of rotation of the output shaft of motor 65 or by varying the cam contour, it is possible to vary the duration of rate of rotary reciprocation of the motor 54.

A slide switch 96 is included in line 92 so that the rotary action of motor 54 can be terminated at any desired time. Thus, not only is the system capable of simultaneous axial reciprocation and rotary reciprocation, but it is also possible to operate with either of the two forms of motion alone. That is, by ceasing operation of motor 44, a simple rotary reciprocation can be imparted through the action of motor 54. Alternatively, by opening switch 96 and closing switch 48, the apparatus can be made to only provide an axial reciprocation.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. Apparatus for opening an obstructed region of a patient blood vessel during an angiographic study, the apparatus comprising:
   a) an angiographic catheter having:
      i) an elongated flexible guidewire with a distal tip for opening the obstructed region and a length sufficient to extend from a region outside a patient to said obstructed region, and,
      ii) a guide means extending along the guidewire for supporting said guidewire for free axial and rotary movement; and,
   b) a power means positioned outside the patient including an output shaft joined to the guidewire, said power means including a motor means for simultaneously axially reciprocating and rotating said guidewire to impart simultaneous axial reciprocation and rotation to the guidewire during said angiographic study.

2. The apparatus according to claim 1 further including control means for varying the rate of axial reciprocation imparted to said guidewire.

3. The apparatus according to claim 2 wherein the power means includes a first motor for rotating said output shaft and a second motor for axially reciprocating said output shaft.

4. The apparatus according to claim 3 wherein said control means includes means for periodically reversing the direction of rotation of said first motor to produce rotary reciprocation of said output shaft.

5. The apparatus according to claim 3 wherein said control means includes a rotary cam for producing periodic reversal of the direction of rotation of said first motor.

6. The apparatus according to claim 1 wherein said angiographic catheter is a coronary dilation catheter.

7. Apparatus for performing an angiographic study and opening an obstructed region of a patient blood vessel during the angiographic study, the apparatus comprising:
   a) an angiographic catheter terminating in a distal tip for abrading and tunneling through the obstructed region of the blood vessel, said angiographic catheter having a guidewire for guiding the catheter through the blood vessel and imparting motion to said distal tip; and,
   b) a power means positioned outside the patient including an output shaft joined to the guidewire, said power means including motor means for simultaneously producing both axial reciprocation and rotary reciprocation of said output shaft.

8. The apparatus as defined in claim 7 further including control means for varying the rate of reciprocation of at least one of said axial reciprocation and said rotary reciprocation.

9. The apparatus as defined in claim 7 further including control means operable for controlling the rate of axial reciprocation of said output shaft.

10. The apparatus as defined in claim 7 wherein said power means includes a first motor for producing said rotary reciprocation of said output shaft and a second motor for producing said axial reciprocation of said output shaft.

11. The apparatus as defined in claim 10 wherein said first motor is mounted for reciprocation and said second motor is drivingly connected to the first motor to reciprocate said first motor.

12. The apparatus as defined in claim 10 further including control means for permitting selective variation in the rate of axial reciprocation produced by said second motor.

13. The apparatus as defined in claim 12 further including a cam for controlling the rate of rotary reciprocation produced by said first motor.

14. The apparatus as defined in claim 13 wherein said cam is adapted to periodically produce reversals in the direction of rotation of said first motor.

15. The apparatus as defined in claim 7 wherein the motor means include a first rotary motor periodically reversed in its direction of rotation.

16. The apparatus according to claim 7 wherein said angiographic catheter is a coronary dilation catheter.

17. A catheter system for performing an angiographic study and opening occluded blood vessels during the angiographic study, the catheter system comprising:
   an angiographic catheter adapted to perform an angiographic study;
   an elongate flexible guidewire disposed within the angiographic catheter and having a length sufficient to extend from a region outside a patient to a blood vessel within the patient, the guidewire including a distal tip extending beyond a distal end of the angiographic catheter for opening occluded blood vessels during the angiographic study; and,
   a power apparatus positioned outside the patient and joined to the guidewire for producing combined rotary reciprocation of the guidewire and axial reciprocation of the guidewire during the angiographic study for guiding the catheter along said blood vessel within the patient and opening occluded blood vessels within the patient.

18. The catheter system according to claim 17 wherein said angiographic catheter is a coronary dilation catheter.

19. The catheter system according to claim 18 further including a control device controlling a rate of said rotary reciprocation of the guidewire and a rate of said axial reciprocation of the guidewire.

20. The catheter system according to claim 19 wherein said control device is adapted to vary said rate of said axial reciprocation of the guidewire without varying said rate of said rotary reciprocation of the guidewire.

21. The catheter system according to claim 20 wherein said power apparatus includes a first motor for rotating said guidewire and a second motor for axially reciprocating said guidewire.

22. The catheter system according to claim 21 wherein said first motor is mounted for reciprocation and said second motor is drivingly connected to the first motor to reciprocate said first motor.

23. The catheter system according to claim 22 wherein said control device includes a cam for controlling the rate of rotary reciprocation of the guidewire produced by the first motor.

24. The catheter system according to claim 23 wherein said cam is adapted to periodically produce reversals in the direction of rotation of the first motor.

25. A method of performing an angiographic study and opening occluded blood vessels during the angiographic study, the method comprising the steps of:
   providing an angiographic catheter adapted to perform an angiographic study and including an elongate flexible guidewire disposed within the angiographic catheter, the guidewire having a length sufficient to extend from a region outside a patient to a blood vessel within the patient, the guidewire including a distal tip extending beyond a distal end of the angiographic catheter for opening occluded blood vessels during the angiographic study;

disposing the catheter within a blood vessel of a patient; and, when an occluded area is encountered by the catheter within said blood vessel, attaching a proximal end of the guidewire to a power apparatus positioned outside the patient and, using the power apparatus, producing combined rotary and axial reciprocation of the guidewire without removing the catheter from the patient during the angiographic study, to guide the catheter along said blood vessel and open said occluded area of said blood vessel.

26. The method according to claim 25 wherein the step of providing said angiographic catheter includes providing a coronary dilation catheter.

* * * * *